United States Patent [19]

Seib et al.

[11] Patent Number: 5,311,768

[45] Date of Patent: * May 17, 1994

[54] MULTI-FACED PROBE AND METHOD OF MEASURING THE STICKINESS OF COOKED STRING PASTA PRODUCTS

[75] Inventors: Paul A. Seib; Feng Guan, both of Manhattan, Kans.

[73] Assignee: Kansas State University Research Foundation, Manhattan, Kans.

[*] Notice: The portion of the term of this patent subsequent to Jan. 25, 2011 has been disclaimed.

[21] Appl. No.: 997,574

[22] Filed: Dec. 28, 1992

[51] Int. Cl.⁵ .................................. G01N 11/02
[52] U.S. Cl. .................. 73/54.22; 73/64.49; 73/169
[58] Field of Search ............... 73/169, 54.22, 150 A, 73/150 R, 64.49

[56] References Cited

U.S. PATENT DOCUMENTS

| | | | |
|---|---|---|---|
| T916,005 | 11/1973 | Dolen et al. | 73/150 A |
| 3,789,660 | 2/1974 | Rubio et al. | 73/169 |
| 4,210,020 | 7/1980 | Wasik | 73/169 |
| 4,437,337 | 3/1984 | Fenrick | 73/54 |
| 4,766,766 | 8/1988 | Ahlert et al. | 73/169 |
| 4,838,081 | 6/1989 | Finley et al. | 73/169 |
| 5,141,767 | 8/1992 | Peterson et al. | 427/8 |

OTHER PUBLICATIONS

Dexter et al.—Grain Research Laboratory Compression Tester: Instrumental Measurement of Cooked Spaghetti Stickiness; Cereal Chemistry, vol. 60 No. 2 1983.
Voisey et al.—Measuring the Texture of Cooked Spaghetti. 2. Exploratory work on Instrumental Assessment of Stickiness and its Relationship to Microstructure; J. Inst. Can. Sci Technol Aliment. vol. 11 No. 4 Oct. 1978.

Primary Examiner—James C. Housel
Assistant Examiner—N. Bhat
Attorney, Agent, or Firm—Hovey, Williams, Timmons & Collins

[57] ABSTRACT

A testing apparatus (20) and a corresponding method are provided for validly measuring the stickiness or adhesiveness of a sample (52) such as cooked pasta. The apparatus (20) includes a support surface (42) on which the sample (52) is placed, an apertured restraining member (106) for preventing separation between the sample (52) and supporting surface (42), a probe (70) presenting a sample-engaging face (82) for engaging and disengaging a portion of the sample (52), and a tester (22) which is coupled to the probe (70) for moving the probe (70) into and out of engagement with the sample (52). A plurality of probes (70-80) may be provided each presenting a different sample-engaging surface (82) for selective and alternate engagement with the sample (52). The restraining member (106) may be mounted on the tester (22) for shiftable movement relative to the sample (52), and is resiliently biased toward the sample (52) for holding the latter firmly against the supporting surface (42). In use, an integrated negative-force region (212) of a force curve generated by the tester (22) is an accurate measure of stickiness of the sample (52).

24 Claims, 5 Drawing Sheets

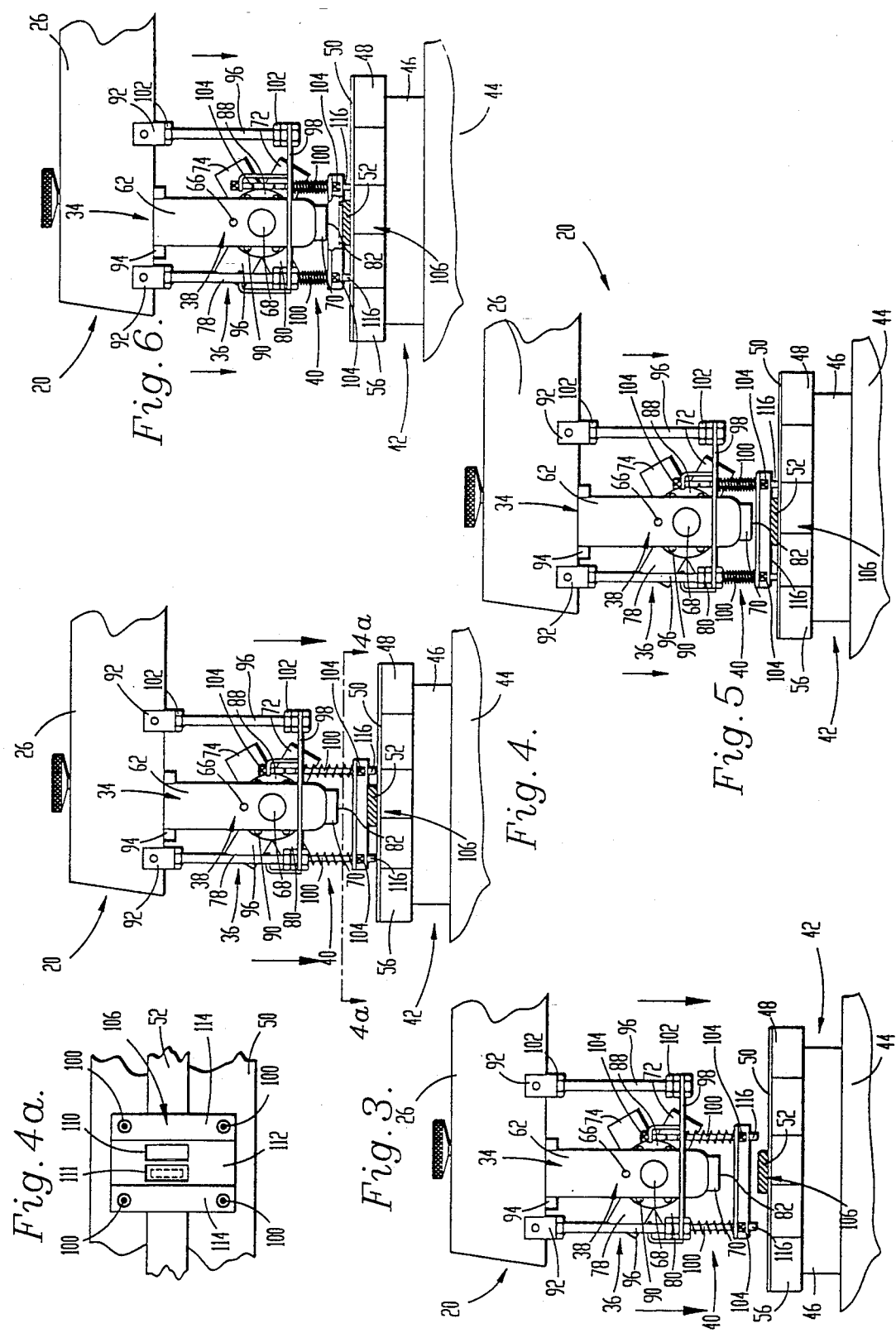

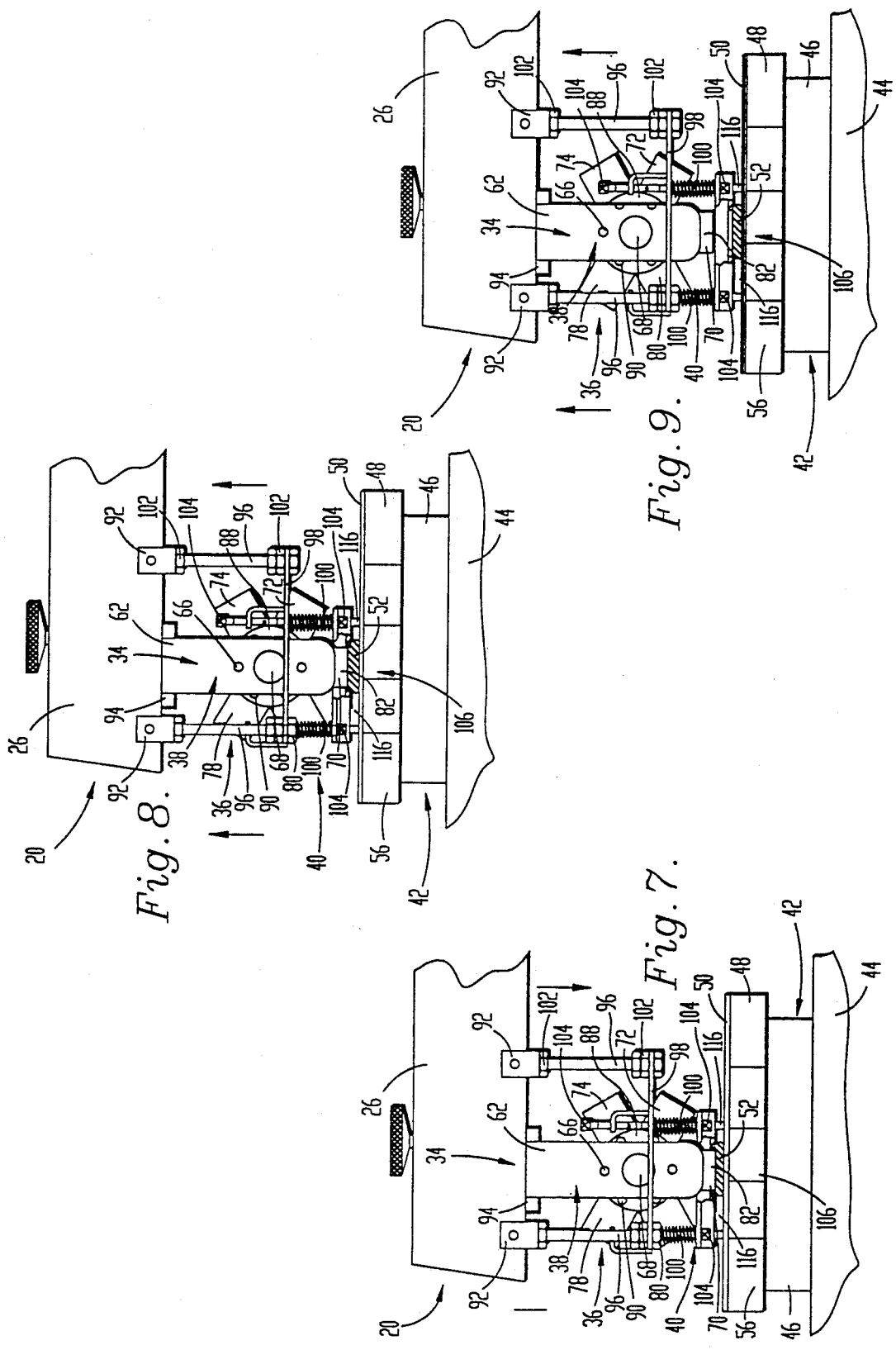

MULTI-FACED PROBE AND METHOD OF MEASURING THE STICKINESS OF COOKED STRING PASTA PRODUCTS

BACKGROUND OF THE INVENTION

1. Field of the Invention

The present invention is broadly concerned with an apparatus and method for testing the stickiness of a sample, i.e. the adhesive force necessary to separate a probe from a sample. More particularly, the invention concerns an apparatus and method whereby a sample is restrained against a supporting surface during engagement and disengagement by the probe, during which the stickiness of the sample is measured. Restraint of the sample insures that the appropriate adhesive force is measured, and eliminates the possibility that the force required to separate the sample from the support surface is being erroneously measured, as opposed to force required to separate the probe from the sample.

2. Description of the Prior Art

The measurement of adhesive properties of various materials has long been considered by the industrial and scientific communities. Testing equipment is readily available which includes a base supporting a sample, together with a probe which can be lowered and compressed against the surface of the sample, and subsequently withdrawn. During the withdrawal or disengagement of the probe from the sample, the adhesive properties, i.e., the force required to separate the probe from the sample, are measured.

More recently, researchers have endeavored to measure the adhesive properties of food samples, such as pasta products of various shapes including elongated spaghetti products. The stickiness of pastas is one factor in determining a product consistency, inasmuch as the stickiness may affect not only the tendency of the pasta pieces to cling together, but also the organoleptic qualities of the product such as taste and texture. The stickiness of cooked pasta products may also be considered as an important indication of the quality of the wheat midlings or flours used in manufacture of the product.

Past efforts to accurately measure the stickiness of pasta products have met with only limited success. In 1978, Voisey et al. described a stickiness test for cooked spaghetti in "Measuring the Texture of Cooked Spaghetti. 2. Exploratory Work on Instrumental Assessment of Stickiness and Its Relationship to Microstructure", reported in the *Canadian Institute of Food Science Technology Journal* Vol. 11, No. 4. The test involved placing strands of cooked spaghetti on a lower serrated plate having 90° V-grooves, compressing the strands with a flat upper plate, and then pulling the flat plate away from the strands at a constant rate while measuring the disengagement force with a load cell. In 1983, Dexter et al. published an article in *Cereal Chemistry* entitled, "Grain Research Laboratory Compression Tester: Instrumental Measurement of Cooked Spaghetti Stickiness". This article reports the use of a Grain Research Laboratory compression tester with a plunger which was moved into and out of engagement with the many spaghetti strands positioned side by side, and used an aluminum retainer plate with an opening for providing plunger to sample access.

A prime difficulty with these prior techniques is that a measurement is taken at one fixed time after cooking, even though surface stickiness changes unpredictably with time. A second difficulty with these methods is due to measurement of the wrong force. When a sample such as cooked pasta is placed upon a support surface and engaged by a probe, lifting of the probe may cause the pasta to separate from the support surface before the probe itself becomes disengaged from the pasta. When this occurs, the force being measured is not a valid measurement of adhesiveness. This is particularly troublesome if pasta separates from the support surface and pasta/probe disengagement occurs on a random or unpredictable basis. This may occur especially when strands of cooked spaghetti or noodles are placed side by side so that water is trapped between and under the strands. A third difficulty is that the former methods rely on a probe with but one type of surface. A probe with multiple types of surfaces and with adjustable surface area would allow the magnification of differences in stickiness. Finally, the old methods are slow and cumbersome with respect to sample preparation and measurement if the operator wishes to make repeated measurements on a sample. Rapid measurement on a single strand of noodle or pasta would permit one to observe changes in stickiness as they occur under ambient room conditions.

SUMMARY OF THE INVENTION

The present invention overcomes the problems outlined above, and provides a greatly improved testing apparatus and method for obtaining valid, reproducible adhesion characteristics or "stickiness" values using a wide variety of samples, and particularly food samples. In addition, multiple, individual samples may be quickly tested on a timed basis, thereby insuring adequate replication for accurate results.

Broadly speaking, the testing apparatus of the invention includes means defining a surface for supporting a sample to be tested, together with means positioned proximal to the sample for engaging it and restraining the sample against separation from the supporting surface; the sample-restraining means includes an element presenting at least one aperture therethrough, together with structure for holding the apertured element in a sample-engaging position adjacent to the support surface. The overall testing apparatus also includes probe means presenting a sample-engaging surface, together with means coupled with the probe for moving the sample-engaging surface toward and through the aperture and into contact with a sample, and for subsequent disengagement of the sample-engaging surface and sample. Finally, means are provided for measuring a parameter correlated with the force required for disengaging the sample-engaging probe surface from the sample.

In preferred forms, the sample-support surface is substantially planar and includes a shrink-resistant filter-paper sheet disposed thereon for resisting transverse movement of the sample. Furthermore, the sample-restraining means is advantageously mounted with the probe for movement of the restraining means toward and into engagement with the supported sample. In order to insure that the sample is properly held for testing purposes, the holding structure associated with the sample-engaging element includes means for resiliently biasing the element against the sample. The preferred sample-engaging element is in the form of an apertured foot plate, and is correlated with the testing surface of the probe so that the probe passes through the foot plate aperture into engagement with the underlying sample.

While the probe may be designed to present only a single testing surface, in preferred forms a probe assembly is provided having a plurality of testing surfaces. To this end, the probe is in the form of a turret having plural, circumferentially spaced test surfaces. The turret is mounted for selective rotation thereof in order to alternately orient each respective test surface relative to a restrained sample for testing purposes.

The probe is operatively coupled with means such as a load cell for accurately measuring a parameter correlated with the force required to disengage the probe testing surface from the restrained sample. Preferably, this parameter can be graphically or digitally displayed, thereby providing an easily understood output.

BRIEF DESCRIPTION OF THE DRAWINGS

FIG. 3 is a fragmentary side view depicting the sample-restraining assembly and probe descending towards a sample to be tested;

FIG. 4 is a view similar to that of FIG. 3 and illustrating initial contact between the sample-restraining assembly and sample, and prior to contact between the probe test surface and sample;

FIG. 4a is a sectional view taken along line 4a—4a of FIG. 4 and illustrating the configuration of the sample-restraining foot assembly;

FIG. 5 is a view similar to that of FIG. 4, and illustrating the sample-restraining assembly with the biasing springs thereof compressed and exerting a proper restraining force against the sample;

FIG. 6 is a view similar to that of FIG. 5, and illustrating the subsequent downward movement of the probe test surface after the sample-restraining assembly is in place;

FIG. 7 is a view similar to that of FIG. 6, and illustrating engagement between the probe test surface and the restrained sample;

FIG. 8 is a view similar to that of FIG. 7, and depicting the initial stages of probe elevation away from the restrained sample;

FIG. 9 is a view similar to that of FIG. 8, but illustrating the probe fully disengaged from the restrained sample;

DESCRIPTION OF THE PREFERRED EMBODIMENT

Figure 2:
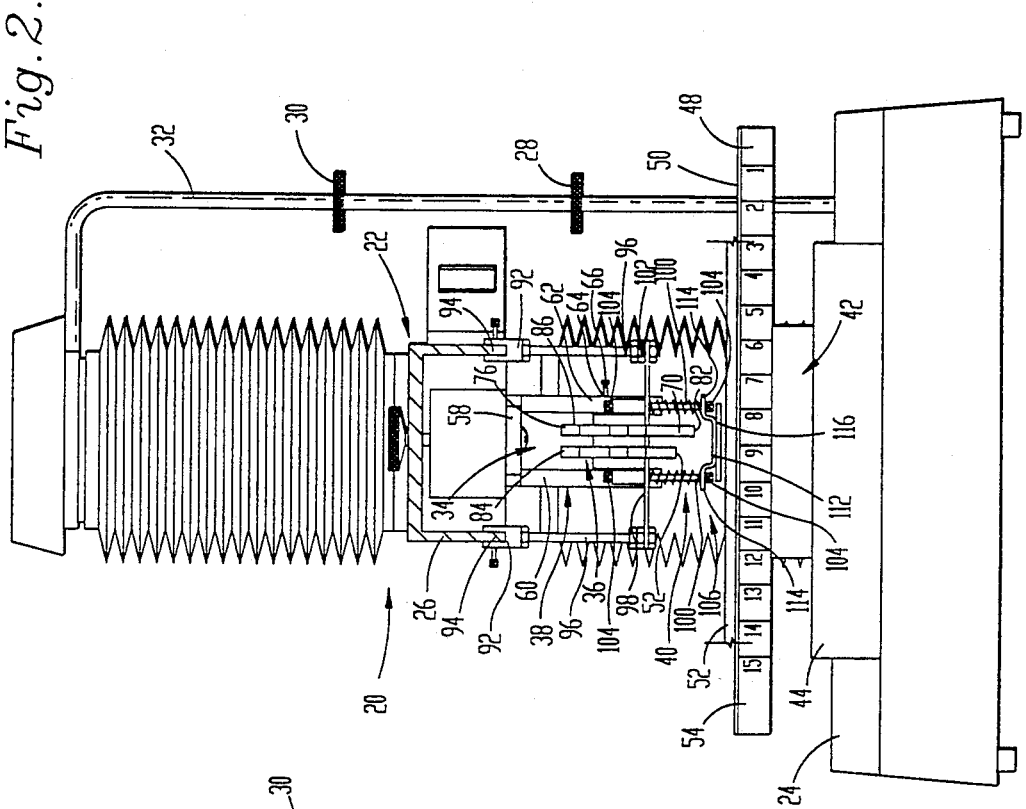
FIG. 2 is a front elevational view of the testing apparatus, illustrating a pasta sample supported on the apparatus base.
Figure 1:
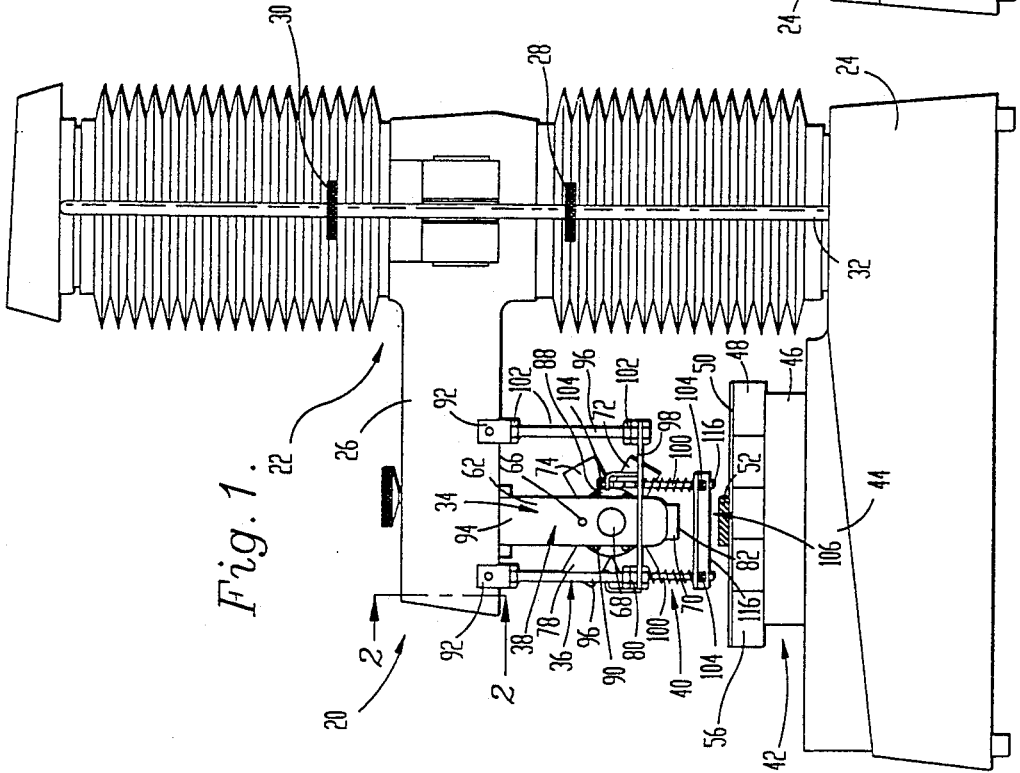
FIG. 1 is a side elevational view of the testing apparatus in accordance with the present invention showing the multiple probe turret and sample-restraining assembly mounted on a beam that also carries the load cell.

Referring now to the drawings and particularly FIGS. 1 and 2, an adhesion or "stickiness" testing apparatus 20 is illustrated. The apparatus 20 includes a commercially available TA.XT2 texture analyzer 22 commercialized by Texture Technologies Corporation of Scarsdale, N.Y. The analyzer 22 includes a base 24 supporting a vertically shiftable, horizontally extending load cell cross arm or beam 26 in an elevated position above the base 24. Movement of the beam 26 is limited by stops 28, 30 located on upright spindle 32, and is controlled through a separate console and stepper motor (not shown). An appropriate recorder (also not shown) is coupled via the console in order to determine and display forces experienced by the load cell.

A probe unit 34 is secured by bolts or the like to the load cell which is attached to the beam 26. The probe unit broadly includes a turret 36 presenting a plurality of circumferentially spaced probes extending radially therefrom and a mount 38 for rotatably holding the turret. The beam 26 also carries a depending, sample-restraining unit 40 which depends somewhat beyond the lowermost probe of turret 36.

The overall testing apparatus 20 further includes a sample support surface 42 positioned on upper test bed surface 44 of base 24 beneath probe unit 34. The support surface includes a pedestal 46, plate 48 and web 50. The web 50 is positioned beneath the sample 52 which is typically, but not necessarily, a precooked pasta noodle. The web 50 is preferably a sheet of Whatman No. 1 chromatography paper which resists shrinkage when wet and inhibits transverse movement of the noodle across the plate 48. The plate 48 is preferably a rectangular sheet of acrylic plastic, plexiglas, or other synthetic resin material which has been numbered in 1.5 cm increments along the side 54 of its longest dimension, with each 1.5 cm distance used as an individual test position. Plate 48 is also marked along the side 56 of its width into five "lanes" corresponding to individual samples when multiple samples are to be tested.

The probe unit 34 and the restraining unit 40 are shown in greater detail in FIGS. 2 and 3-9. Mount 38 includes a head 58 and a pair of spaced-apart legs 60 and 62. The head 58 is bolted to the load cell connected to the beam 26, and one of the legs, such as leg 62, includes at least one threaded hole 64 for threadably receiving a stop screw 66 therein. Each leg 60 and 62 is also apertured to receive an axle 68 therethrough on which turret is rotatably mounted.

Turret 36 includes a plurality of radially extending probes 70, 72, 74, 76, 78, and 80 thereon. Each probe preferably presents a different sample-engaging surface 82, and may be configured as a pair of side-by-side probe elements 84 and 86 as shown in FIG. 2. For example, when a flat ribbon of pasta is the sample, the probe preferably presents a substantially flat surface 82. The remote margin 82 of a probe might also include a Teflon coating or be roughened to simulate different surfaces with which the sample might come into contact.

The turret 36 also includes a central hub 88 which is preferably integrally formed with the probes 70, 72, 74, 76, 78 and 80 of a clear synthetic resin material such as plexiglas so that each probe may be substantially uniform except for the differences in configuration of the corresponding surface 82. A series of cavities 90 are provided in the hub in alignment with each probe. Each cavity is configured and positioned to receive the stop screw 66 therein for selectively locking the turret 36 with the desired probe (e.g., probe 70 in the drawing) in sample-engaging orientation and against undesired rotation thereof and thus movement out of alignment.

The restraining unit 40 is coupled to the beam 26 by four support mounts 92 each attached by a set screw to the beam 26. A spacer rod 96 depends from each support mount 92, with the rods 96 carrying a suspension table 98 at the lower ends thereof. The suspension table 98 serves to provide a suitable support base for carrying suspension rods 100 therefrom. The spacer rods 96 are threaded at the respective ends thereof and held in place by nuts 102, while knurled nuts 104 are threaded onto each lower end of the suspension rods 100.

Restraining foot 106 is positioned remotely from beam 26 and is biased downwardly toward the sample 52 by springs 108 mounted on suspension rods 100. The springs 108 are individually mounted on each suspension rod 100 between the suspension table 98 and restraining foot 106. The knurled nuts 104 at the bottom of the suspension rods serve to limit the travel of the restraining foot 106 toward the sample. The restraining foot 106 defines a pair of apertures 110, 111 therethrough for permitting the surface 82 of the probe in alignment therewith to pass through, and in fact is of a size such that each probe is free to pass through an aperture 110, 111 without engaging the surrounding restraining foot 106; nevertheless, the surrounding restraining foot 106 is positioned close to the probe to inhibit separation of the sample 52 from the support web 50.

The restraining foot 106 includes a substantially flat sample-engaging floor 112 surrounding the aperture 110, a pair of shoulders 114 for receiving the suspension rods 100, and rails 116. While the sample 52 normally engages the floor 112, the rails 116 prevent excessive compression of the sample. Excessive compression of the sample may lead to destruction and alteration of the ability to test the stickiness of the outer surface. Those skilled in the art will appreciate that other, differently configured rails may be selectively used in lieu of the rails 116, in order to accommodate products of different thicknesses.

The operation of the testing apparatus 20 is illustrated by the steps shown in FIGS. 3–9. After the sample is initially prepared, it is placed on the support surface 42 of the testing apparatus where a web 50 has been placed on the plate 48 and then held in place by clamps. The texture analyzer 22 serves as a testing means to measure the force necessary to separate the probe from the sample. After the sample is positioned in the testing apparatus 20, the texture analyzer is actuated to begin movement of the beam 26.

In FIG. 3, the beam 26 is in the "up" position whereby neither the restraining foot 106 nor the desired probe 70 is in engagement with the sample. Thus, the restraining foot 106 is biased toward its fully remote position away from the beam and toward the sample 52. The beam 26 moves upwardly and downwardly at a constant, controlled speed for each phase of the testing operation, so that time as recorded may be readily converted into distance. In the downward motion phase prior to engagement of the probe 70 with the sample 52, the arm moves downward at a rate of 1 mm/sec. In FIG. 4, the beam has moved downward a sufficient distance that the restraining foot 106 engages the sample 52 and begins to press the sample against the support surface 42. However, the springs 108 are yieldable so that the suspension rods 100 and restraining foot 106 remain stationary while the probe unit 34 moves downwardly with beam 26, as illustrated by FIG. 5.

FIG. 6 shows the probe 70 just prior to passing through the aperture 110 of restraining foot 106. The springs 108 cause the restraining foot 106 to exert an increasing force against the sample 52 as the beam 26 carrying the probe unit 34 and the restraining unit 40 moves toward the sample 52. The web 50 inhibits any sliding or lateral movement of the sample, which may tend to slip if in direct contact with the plate 48.

Figure 10:
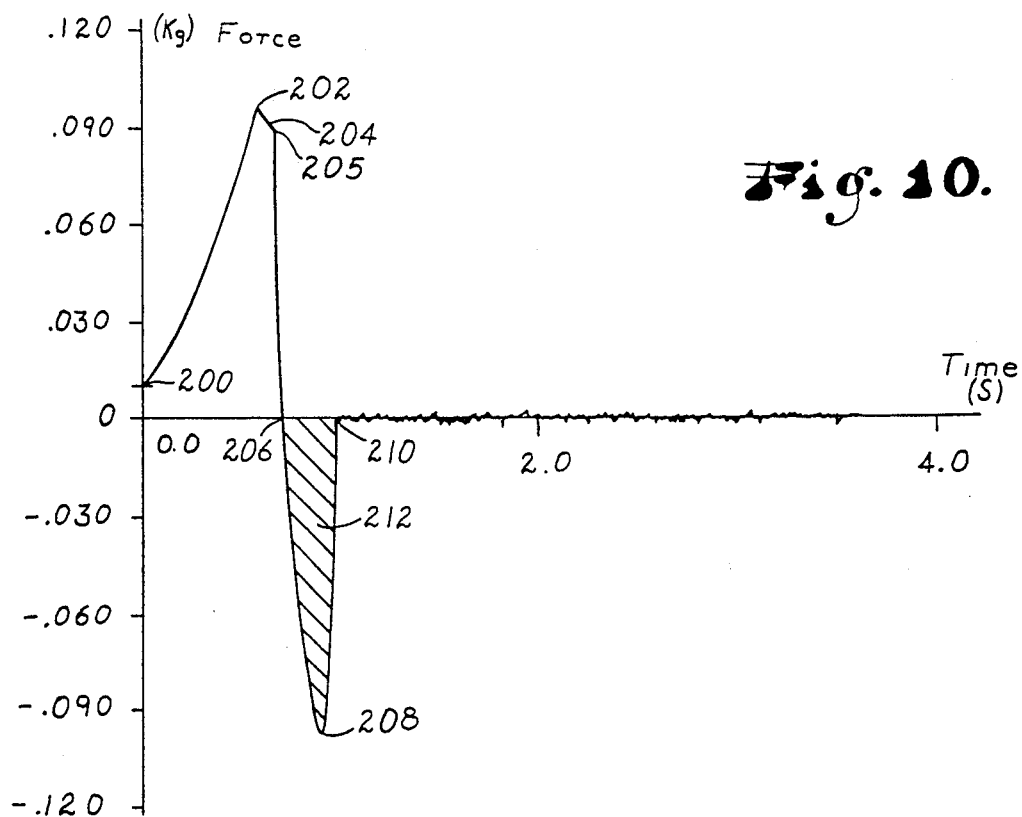
FIG. 10 is a typical graph of stickiness testing results for a pasta sample, wherein force in kilograms-force is plotted versus time in seconds.

FIG. 7 shows the surface 82 of probe 70 engaging the sample 52. As the probe 70 first engages the sample 52, the texture analyzer begins to sense a positive force on the probe, as shown in FIG. 10. The maximum force on the probe must be optimized for a given product, and is set by the operator. Too little force gives poor contact between the probe surface and sample, whereas excessive force changes the surface of the sample. In the case of noodle and spaghetti strands, a maximum force of 100 grams gives reproducible stickiness measurements. When the positive force is detected at point 200 on the graph of FIG. 10, the beam preferably slows to a speed of 0.1 mm/sec. The positive force experienced by the load cell associated with the beam increases until reaching maximum peak 202 on the FIG. 10 graph, at which point movement of the probe ceases. Thereafter, the experienced force begins to diminish as the sample 52 undergoes momentary relaxation to point 204. After point 202, the probe has fully engaged and become adhered to the sample 52, and there is a monetary pause during which the probe and arm remain stationary. Then at point 204, the beam 26 reverses to the retraction mode depicted in FIG. 8, which is preferably at a faster rate of 3 mm/sec. FIG. 8 further illustrates that the portion of the sample 52 may actually be pulled into the confines of aperture 110 by beam reversal; however, the sample normally stays below the upper surface of the foot 106.

The essentially vertical line below point 205 in the FIG. 10 graph illustrates that the force experienced by the beam load cell is rapidly dropping to zero (point 206) and then to a negative value having its negative maximum at point 208, as the beam is moved upwardly and is subjected to a pulling or tensile force. The portion of the graph betweens points 208 and 210 indicates that separation between the sample and probe surface has occurred, and that the force experienced by the beam load cell rapidly moves from the maximum point 208 to the zero force point 210.

The adhesion between the surface 82 of probe 70 and the sample 52 is measured in kilograms-force as the total integrated area 212 below the zero line of the graph and bounded by the points 206, 208 and 210. In this respect, the rapid upward or reversal movement of the beam 26 is important to insure that adhesion forces are accurately measured. Slow retraction with certain samples may allow the elasticity in the sample to be sensed by the probe, thereby distorting the measurements of stickiness or adhesion.

It will also be appreciated that during the retraction of the beam 26, the restraining foot 106 remains in biased engagement with sample 52, in order to insure that the sample is firmly held against web 50.

After the adhesion characteristics are measured, the beam 26 continues its upward movement as shown in FIG. 9, to the point where the entire apparatus separates from the underlying sample, and the analyzer reassumes the position shown in FIG. 3.

In determining the adhesive force of a sample such as pasta, it is imperative that all specimens be treated substantially the same and measured for stickiness as close in time as possible. In testing cooked pasta with the present invention, it is desirable to measure the pasta sample at the maximum stickiness, which varies with the length of time from the removal of the pasta from boiling water. In the adhesion tests reflected in FIGS. 11 and 12, pasta samples made from durum and hard winter wheat were employed. Specifically, distilled water was added to the respective flour samples, as determined by handling and appearance properties, to a moisture content of about 33% by weight, wet basis. The respective doughs were then covered and allowed to rest for a 15 minute period, whereupon noodles were formed using a pasta press, by extruding each dough at 35° C. through a die having 6 mm×0.5 mm openings. The extruded noodles were then cut into lengths of about 50–60 cm, and allowed to dry as follows: one period at 30° C. for 15 minutes and 90% relative humidity; three periods each at 45° C. for four hours and 85%, 80%, and 75% relative humidity, respectively, and a final period at 30° C. for 15 minutes and 75% relative humidity. The dried noodles, which had a final, dried width of about 5.6 mm and a thickness of about 0.6 mm, were equilibrated to room conditions for 24 hours, packed in polyethylene zip-lock bags, and stored in a cabinet at room temperature until cooked.

Individual pasta noodles (210 mm in length, 5.6 mm in width, and 0.6 mm in thickness) were then added to 2000 ml of boiling distilled water in an aluminum pan. While distilled water was used in these tests set forth herein, tap water or artificially hard water may be used. Each noodle was cooked for 2.5 minutes. Other strands were cooked individually in the same manner at 1 minute intervals. After cooking, each noodle was immersed in 200 ml distilled water and allowed to stand for 1.5 minutes. Upon removal, the average dimension of the strands changed to 256 mm in length, 7.6 mm in width, and 0.8 mm in thickness. The strands were then mounted on the paper web 50 (previously clamped to plate 48) in a spaced array extending lengthwise, and allowed to rest for 10 minutes. The loaded plate 48 was then placed on the test bed of the texture analyzer 22 and the mounted strands were then tested for stickiness or adhesion force by the probe in accordance with the procedure set forth above. After each measurement, the negative force-time (and because the rate of movement of the probe during retraction was constant, the negative force-distance) curve was integrated and stored in the memory of a computer. Advantageously, the device 20 permits 5 or more strands to be measured in rapid sequence to avoid variances due to different aging times and ensures that the strands remain in contact with the support surface during withdrawal or retraction of the probe 70.

Figure 11:
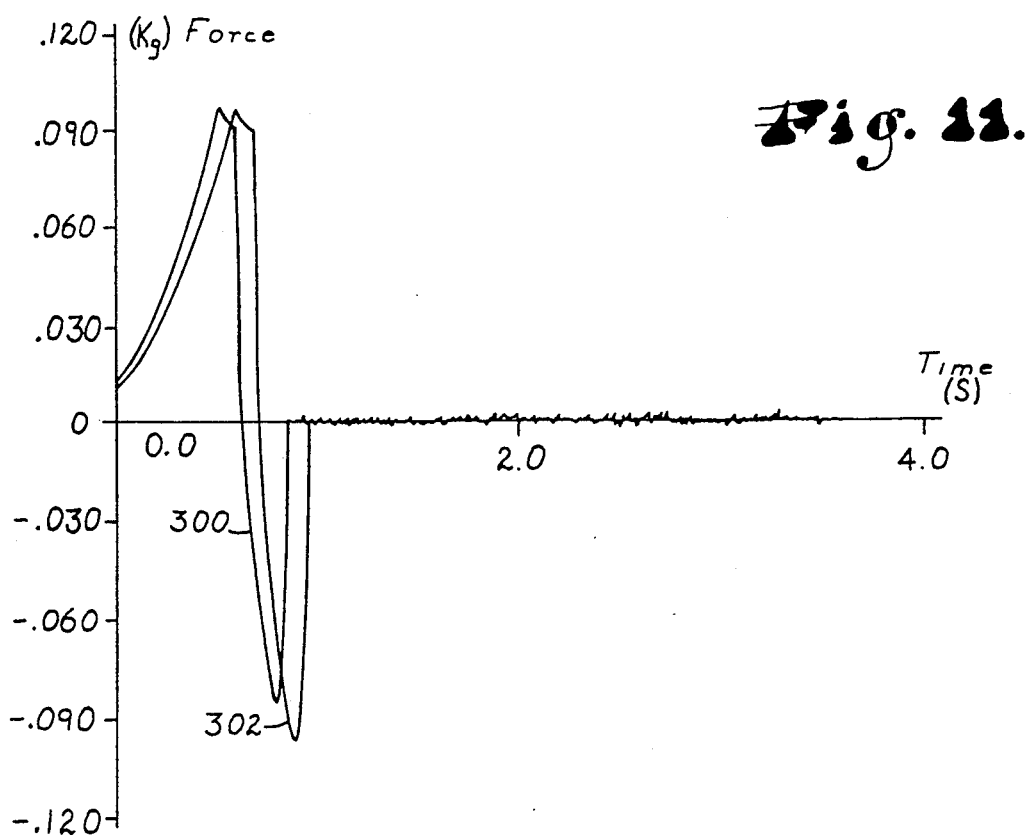
FIG. 11 is a graph similar to that of FIG. 10, and shows comparative results obtained with cooked noodles made from Durum flour and hard winter wheat flour.
Figure 12:
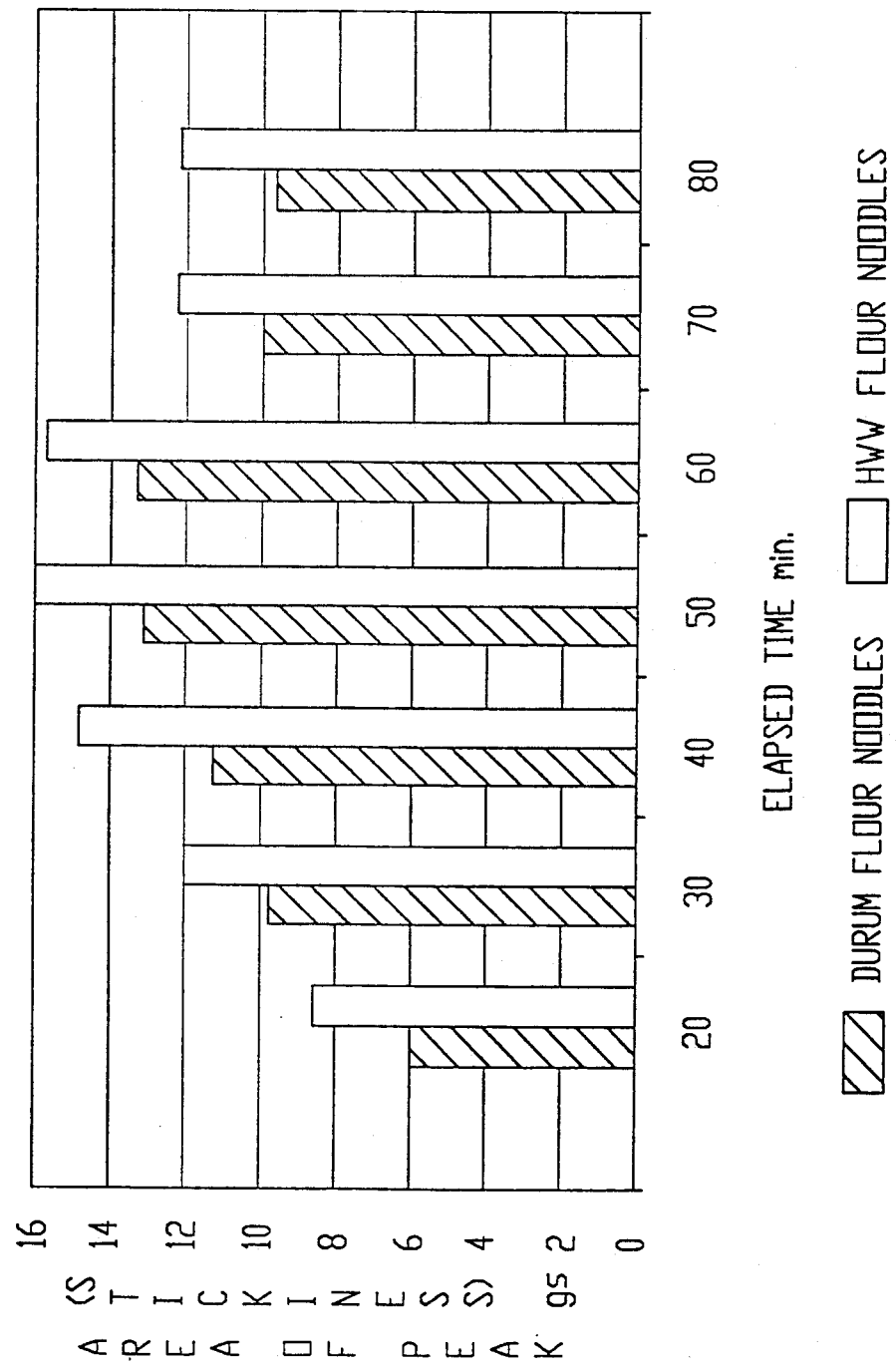
FIG. 12 is a bar graph illustrating calculated work values obtained by testing cooked Durum flour and hard winter wheat flour pastas at different elapsed periods after cooking.

The measurements and integration of the stickiness curve was performed for each sample. FIG. 11 illustrates the difference between the measured adhesion force in kilograms-force versus time (and thus distance as the rate of retraction was constant) for two representative samples. Curve 300 represents the stickiness curve for a noodle formed from durum, while curve 302 represents the stickiness curve for a noodle formed of hard winter wheat. The steps of engaging the sample with the probe and then withdrawing the probe, measuring the adhesive force, and then integrating the negative portion of the curve representing the adhesive force to obtain the work performed were repeated at unperturbed positions along the length of each strand every 10 minutes. The plot of the integrated negative curve values representing stickiness against the time of aging the cooked noodle samples is set forth in FIG. 12, reflecting that the peak stickiness occurred at an aging time of 50 minutes. However, it will also be appreciated that the relative stickiness of the samples made from the two different flours remained substantially the same throughout the test.

The testing device 20 hereof enables the testing of several different configurations of samples, such as pasta samples, in rapid succession so that time does not affect the results. For example, the surface area of the remote margin 82 can be measured in advance for each different configuration to be engaged. In this manner, the adhesion force and calculated work can be compared by factoring in the area of the sample to be engaged. These results can then be effectively compared with flat pasta specimen such as fettucini where the force or work can again be divided by the area of engagement. Thus, adhesive force for different samples 52 from the same or different flours can be compared.

We claim:

1. A method of measuring the adhesiveness of a sample, comprising the steps of:
   providing a supporting surface;
   placing the sample in contact with the supporting surface;
   positioning an apertured restraining member in engagement with the sample for holding the sample against separation from the supporting surface, and with a portion of the sample adjacent the aperture presenting a test region;
   providing a sample-engaging probe presenting an adhesion surface;
   shifting said probe toward and through said apertured restraining member and into engagement with said test region of said sample, and causing adherence between the probe and test region;
   shifting said probe out of engagement with said test region; and
   measuring a parameter correlated with the force required for disengaging said probe from said test region.

2. The method as set forth in claim 1, including the steps of first shifting said restraining member into said engagement with said sample, and thereafter shifting said probe into and out of engagement with said test region through said aperture.

3. The method as set forth in claim 1, said sample comprising a cooked dough product.

4. The method as set forth in claim 1, including the step of calculating the total work required for disengagement of said probe from said sample.

5. Testing apparatus for measuring adhesion of a sample comprising:
   means defining a surface for supporting said sample thereon;
   means positioned proximal to the sample for engaging the sample and restraining the same against separation from said supporting surface, said sample-restraining means including an element presenting at least one aperture therethrough, and a surface for engaging and holding said sample against said supporting surface;
   probe means including a sample-engaging surface configured for passage through said aperture and into contact with said sample;
   means operatively supporting said sample-engaging means and said probe means above said surface, including means operably coupled with said probe means for selective sample testing movement of said sample-engaging surface toward and through said aperture and into contact with said sample therebelow, and for disengagement of said sample-engaging surface and sample; and means operably coupled with said probe for measuring a parameter correlated with the force required for disengaging said sample-engaging surface from said sample.

6. Testing apparatus as set forth in claim 5, wherein said sample-supporting surface is substantially planar and includes a covering for resisting transverse movement of the sample thereon.

7. Testing apparatus as set forth in claim 6, wherein said covering comprises a sheet of shrink-resistant material resting atop said sample-supporting surface.

8. Testing apparatus as set forth in claim 7, wherein said sheet is composed of paper.

9. Testing apparatus as set forth in claim 5, including structure operably coupled with said restraining means for shifting movement thereof toward and away from said sample-supporting surface.

10. Testing apparatus as set forth in claim 5, including means for resiliently biasing said element against said sample.

11. Testing apparatus as set forth in claim 10, said element comprising a foot plate.

12. Testing apparatus as set forth in claim 5, said probe including structure defining a plurality of respective different sample-engaging surfaces each being selectively movable to an operative position for said sample testing movement thereof.

13. Testing apparatus as set forth in claim 5, wherein said sample-engaging surface is complementally configured with the portion of the sample engaged thereby.

14. Testing apparatus as set forth in claim 5, said element presenting a face opposed to said sample-engaging face, the upper surface of said sample being below said opposed face when the sample-restraining means is in operative engagement with said sample.

15. Testing apparatus as set forth in claim 5, said measuring means being operable for measuring the force required for disengaging said sample-engaging surface from said probe.

16. Testing apparatus for measuring adhesion of a sample comprising:
means defining a support surface for receiving the sample thereon;
probe means including a sample-engaging surface;
means for engaging said sample and restraining the same against separation form said support surface;
means for shifting said sample-restraining means into contact with said sample, and for subsequently moving said probe into and out of engagement with the sample after the sample is contacted by the sample-restraining means, including means for operatively supporting said sample shifting means and said probe means above said surface; and
means operably coupled with said probe for measuring a parameter correlated with the force required for moving said sample-engaging surface out of engagement with said sample.

17. Testing apparatus as set forth in claim 16, including structure for biasing said sample-restraining means against said sample during contact between the sample-restraining means and the sample.

18. Testing apparatus as set forth in claim 16, said sample-restraining means comprising an apertured element.

19. Testing apparatus as set forth in claim 18, said element being a plate, said sample-engaging surface of said probe means being configured for passage through said aperture and into engagement with said sample.

20. Testing apparatus for measuring adhesion of a sample comprising:
means defining a surface for said sample thereon;
probe means including a plurality of respective, sample-engaging surfaces;
means supporting said probe means for selectively and alternately placing each of said sample-engaging surfaces in a testing orientation adjacent said sample-supporting surface;
means operatively supporting said sample-engaging surface and said probe means, including means operably coupled to said probe means for selective sample testing movement thereof in order to cause the respective sample-engaging surface thereof in said testing orientation to move into and our of contact with said sample; and
means coupled with said probe for measuring a parameter correlated with the force required for disengaging said respective sample-engaging surface from said sample.

21. Testing apparatus as set forth in claim 20, including means positioned proximal to said sample for engaging the sample and restraining the same against separation from said support surface.

22. Testing apparatus as set forth in claim 21, said sample-engaging means including an apertured foot plate.

23. Testing apparatus as set forth in claim 22, each of said sample-engaging surfaces being configured for passage through said apertured foot plate in order to contact said sample.

24. Testing apparatus as set forth in claim 20, said probe supporting structure including means rotationally mounting said probe for permitting selective rotation thereof in order to selectively and alternately place each respective sample-engaging surface in said testing orientation.

* * * * *

UNITED STATES PATENT AND TRADEMARK OFFICE
CERTIFICATE OF CORRECTION

PATENT NO. : 5,311,768

DATED : May 17, 1994

INVENTOR(S) : PAUL A. SEIB and FENG GUAN

It is certified that error appears in the above-identified patent and that said Letters Patent is hereby corrected as shown below:

On the title page, in item [*] Notice, delete the present notice and substitute the following:

--The term of this patent shall not extend beyond the expiration date of Pat. No. 5,280,717.--.

Signed and Sealed this

Thirtieth Day of January, 1996

Attest:

BRUCE LEHMAN

Attesting Officer

Commissioner of Patents and Trademarks